(12) United States Patent
Cowart et al.

(10) Patent No.: US 10,865,017 B1
(45) Date of Patent: Dec. 15, 2020

(54) MOLD FOR MAKING CANISTER LID

(71) Applicant: DeRoyal Industries, Inc., Powell, TN (US)

(72) Inventors: Walter C. Cowart, Blaine, TN (US); Randall Harris, Knoxville, TN (US)

(73) Assignee: DeRoyal Industries, Inc., Powell, TN (US)

( * ) Notice: Subject to any disclaimer, the term of this patent is extended or adjusted under 35 U.S.C. 154(b) by 0 days.

(21) Appl. No.: 16/773,124

(22) Filed: Jan. 27, 2020

Related U.S. Application Data

(62) Division of application No. 16/008,794, filed on Jun. 14, 2018.

(51) Int. Cl.
*B29C 45/00* (2006.01)
*B65D 43/02* (2006.01)
*A61M 1/00* (2006.01)

(52) U.S. Cl.
CPC ...... *B65D 43/0237* (2013.01); *B29C 45/0017* (2013.01); *B29C 45/0081* (2013.01); *A61M 1/0001* (2013.01); *B65D 2401/15* (2020.05)

(58) Field of Classification Search
CPC ............ B65D 43/0237; B65D 2401/15; B65D 41/48; B65D 2401/35; B29C 33/42
See application file for complete search history.

(56) References Cited

U.S. PATENT DOCUMENTS

| 4,474,302 | A |   | 10/1984 | Goldberg et al. |
| 4,691,501 | A | * | 9/1987 | King ..................... B65B 7/2842 221/222 |
| 5,725,115 | A |   | 3/1998 | Bosl et al. |
| 5,931,332 | A | * | 8/1999 | Mygatt ............... B65D 43/0239 220/270 |
| 5,960,837 | A |   | 10/1999 | Cude |
| 7,806,879 | B2 |   | 10/2010 | Brooks et al. |
| D641,866 | S |   | 7/2011 | Burgess et al. |
| D644,317 | S |   | 8/2011 | Tsao |
| 8,172,832 | B1 |   | 5/2012 | Gonzalez |
| D678,502 | S |   | 3/2013 | Schmidt et al. |
| D679,807 | S |   | 4/2013 | Burgess et al. |
| D679,943 | S |   | 4/2013 | Zhou |
| D687,943 | S |   | 8/2013 | Kobayashi et al. |
| 8,887,770 | B1 |   | 11/2014 | Shippert |
| 9,033,943 | B2 |   | 5/2015 | Stubber |
| D808,037 | S |   | 1/2018 | Gavlak et al. |
| D835,778 | S |   | 12/2018 | Mozzicato et al. |
| D836,774 | S |   | 12/2018 | Ross et al. |
| D837,976 | S |   | 1/2019 | Kaye et al. |
| D839,421 | S |   | 1/2019 | Baldauf et al. |
| 2005/0067735 | A1 | * | 3/2005 | Kaufman ................ B29C 43/14 264/245 |

(Continued)

*Primary Examiner* — Joseph S Del Sole
*Assistant Examiner* — Mohamed K Ahmed Ali
(74) *Attorney, Agent, or Firm* — Luedeka Neely Group, PC (57) ABSTRACT

A mold for forming a lid having a cap connected to the lid by a tether. The mold has mold features for forming a lid body having a peripheral edge, a cap, a tether connecting the cap to the lid body, and a tear zone. The mold feature for forming the tear zone includes an elongate ridge located between the mold feature for the tether and the mold feature for the lid body for providing a reduced thickness flow path proximate the ridge that connects between the mold feature for forming the lid body and the tether.

1 Claim, 9 Drawing Sheets

(56) References Cited

U.S. PATENT DOCUMENTS

2011/0139667 A1    6/2011  Burgess et al.
2015/0216342 A1*  8/2015  Tabor .................... B65D 43/02
                                                 220/254.3

\* cited by examiner

MOLD FOR MAKING CANISTER LID

FIELD

This disclosure relates to the field of medical suction devices. More particularly, this disclosure relates to an improved disposable lid for medical suction canisters.

BACKGROUND

Improvement is desired in the construction and molding of disposable plastic lids for medical suction canisters. The plastic material used in the molding of disposable lids represents a significant cost in the manufacture of such lids. Conventional lids are of a structure that incorporates substantial excess plastic, representing both waste and excess material cost. The molds and methods used in molding the lids contributes to this, as one limiting factor in the molding of lids is the avoidance of excess molding time and unacceptably high injection pressures.

For example, conventional tethered caps on canister lids utilize relatively thick tethers, as the tether path provides the path for the flow of plastic used to form the relatively larger cap part. The tether path provides a relatively large plastic flow path that facilitates molding of the larger cap part at the end of the tether. Such thick tethers are often ⅛ inch or greater in width and ⅛ inch or greater in thickness, for example. However, the thick tethers are not only wasteful of plastic, they are cumbersome, stiff and make the lids difficult to package, transport and store. An example of such a lid having a thick tether is shown in U.S. Pat. No. 7,806,879.

What is desired is a disposable lid that requires substantially less plastic in its manufacture, and for a process and mold for molding such lids having tethered caps that avoid undesirable molding times, unacceptable high pressures, and provide an improved tether structure and avoids the disadvantages of thick tethers.

SUMMARY

The above and other needs are met by an improved lid construction.

In one aspect, a lid according to the disclosure is of molded plastic construction and includes a lid body and a cap attached to the lid body by a tether. The tether is substantially continuous with an adjacent peripheral edge of the lid body, with a tear zone between the tether and the adjacent peripheral edge of the lid body formed during molding of the lid. The tear zone is disruptable by application of a tearing pressure to free the tether from the peripheral edge.

In another aspect, a lid according to the disclosure includes a lid body; a plurality of caps; and a plurality of tethers. Each tether is attached to one of the caps to locate the caps at spaced apart locations about a periphery of the lid body. Each tether is also substantially continuous with an adjacent peripheral edge of the lid body and has a tear zone between the tether and the adjacent peripheral edge of the lid body formed during molding of the lid.

In a further aspect, the disclosure provides a mold for forming a lid having a cap connected to the lid by a tether. The mold has mold features for forming a lid body having a peripheral edge, a cap, a tether connecting the cap to the lid body, and a tear zone. The mold feature for forming the tear zone includes an elongate ridge located between the mold feature for the tether and the mold feature for the lid body for providing a reduced thickness flow path proximate the ridge that connects between the mold feature for forming the lid body and the tether.

BRIEF DESCRIPTION OF THE DRAWINGS

Further advantages of the disclosure are apparent by reference to the detailed description when considered in conjunction with the figures, which are not to scale so as to more clearly show the details, wherein like reference numbers indicate like elements throughout the several views, and wherein.

DETAILED DESCRIPTION

With reference to the drawings, there is shown a canister lid 10 according to the disclosure. The canister lid 10 provides a lid body 10a of molded plastic construction and includes a plurality of caps 12 attached to the lid by tethers 14. A unique aspect of the lid 10 relates to the structure and manner of formation of the tethers 14.

The structure and manner of formation of the tethers 14 enables manufacture of a disposable lid that requires less plastic in its manufacture than is utilized in making conventional lids.

In addition, the process and mold utilized for molding such lids according to the desire enable reduced molding times due to the use of less plastic in forming the tethers. The process also avoids high molding pressures typically associated with the molding of conventional lids of the type previously noted having thick tethers.

Moreover, the resulting lids offer an improved tether structure that avoids the disadvantages of thick tethers. The lids are also advantageous in that they are easier to package, transport and store than conventional lids. Further, the resulting lids have improved aesthetics and a desirable appearance as compared to conventional lids.

Figure 1:
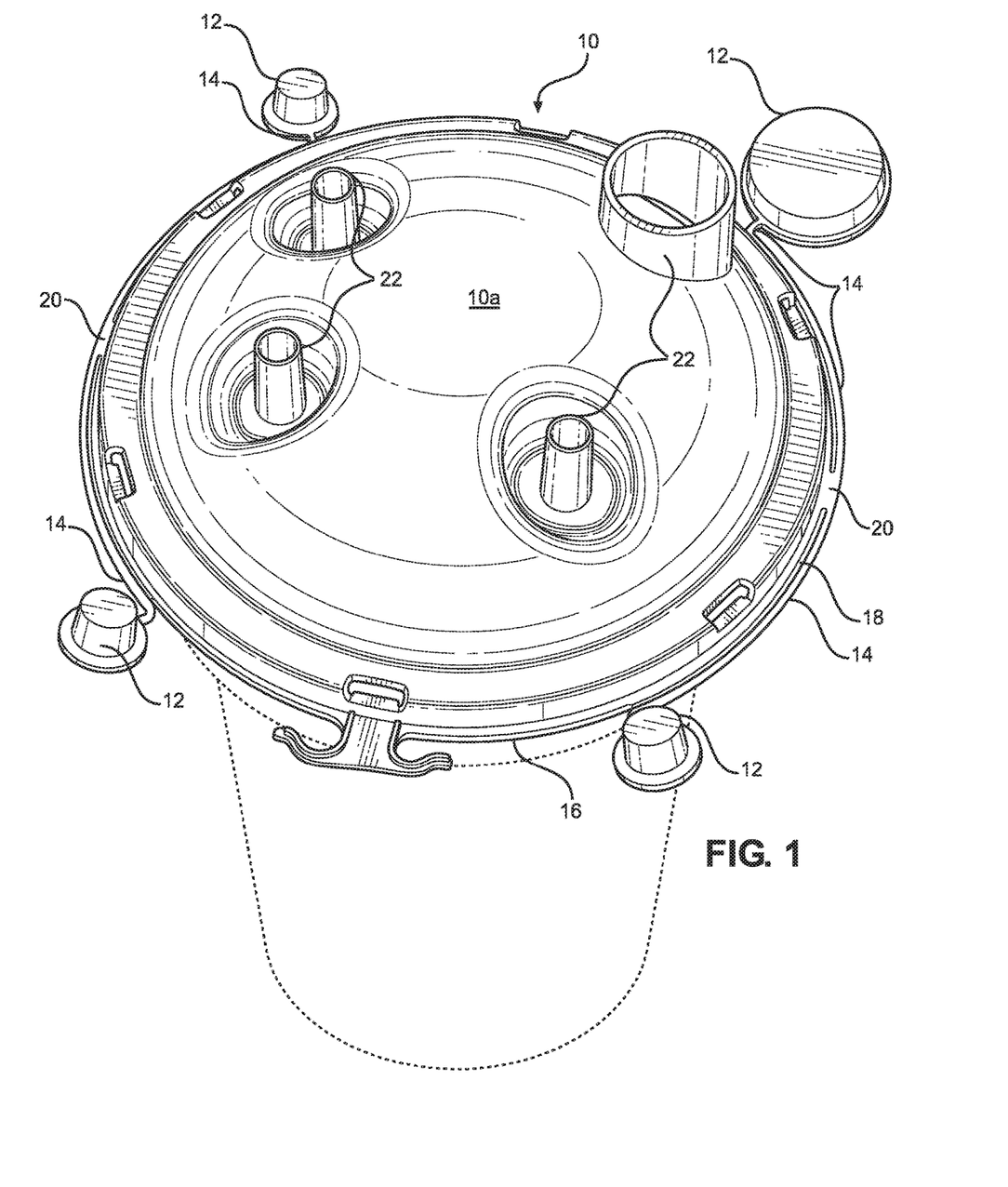
FIG. 1 is a perspective view of a canister lid according to the disclosure, having tethered caps.
Figure 3:
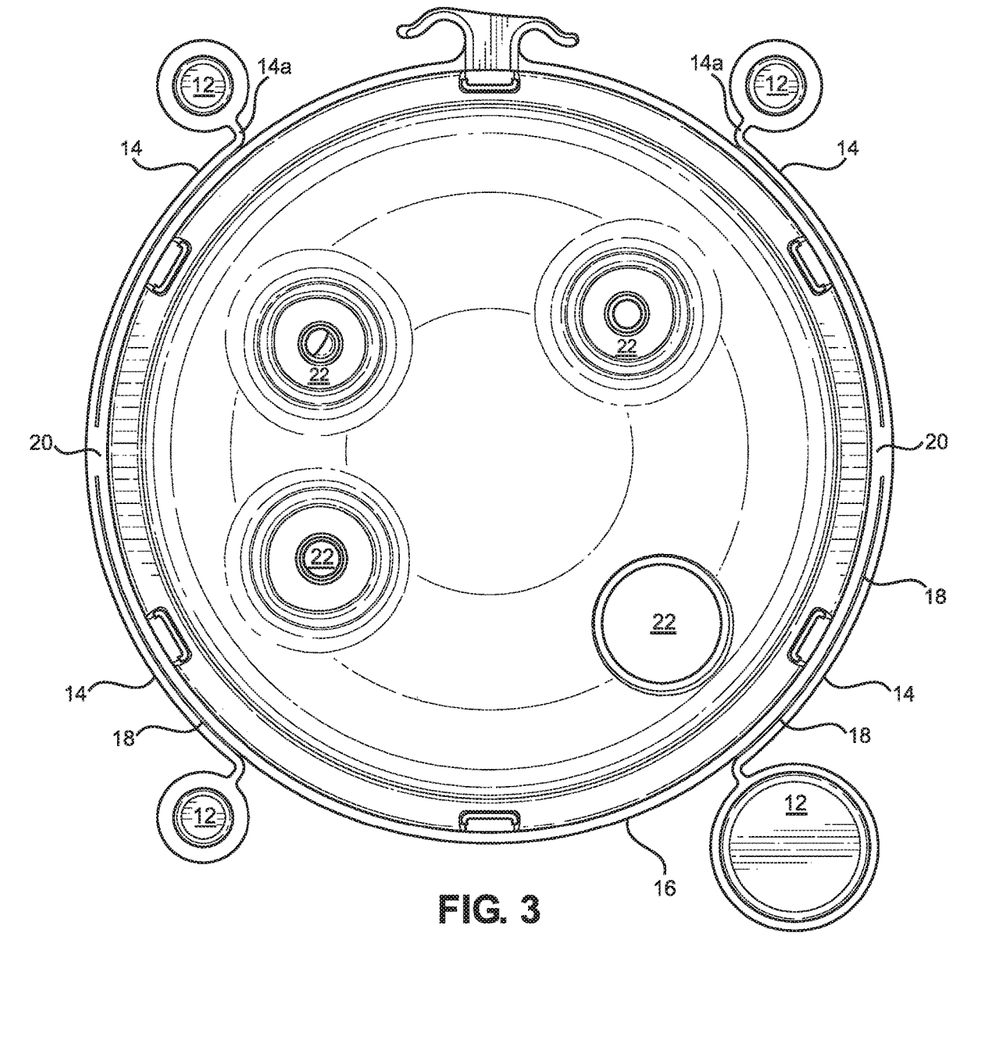
FIG. 3 is a top view of the cap of FIG. 1.
Figure 4:
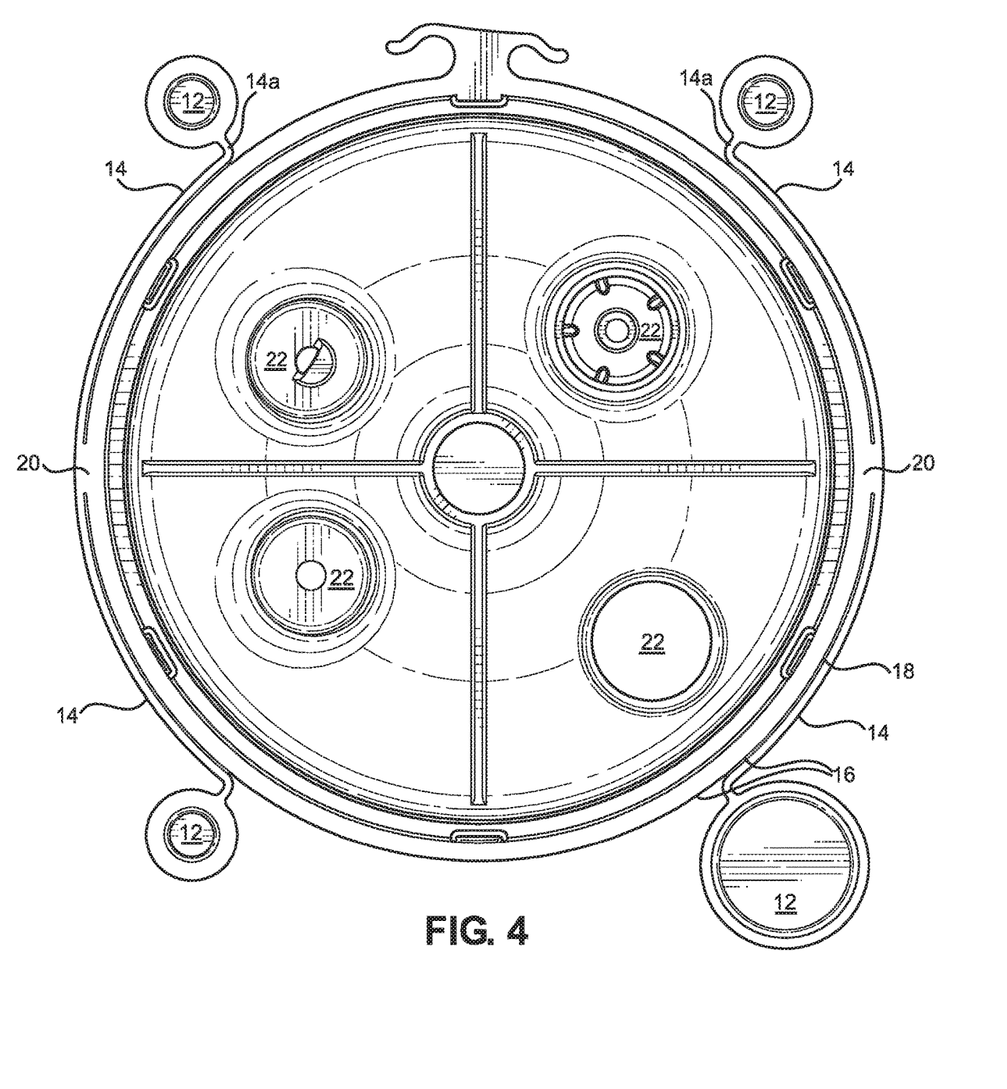
FIG. 4 is a bottom view of the cap of FIG. 1.

FIGS. 1, 3 and 4 show the lid 10 with the caps 12 and tethers 14 as molded. The tethers 14 of the completed lid 10 are continuous with peripheral edges 16 of the lid 10. Between the edges 16 and the tethers 14 are tear zones 18. The tear zones 18 may be continuous as shown or segmented as shown in the alternate embodiments of FIGS. 7 and 8.

For the embodiment of FIGS. 1-6B, the tear zones 18 are provided as thin and narrow zones of plastic that render the tethers 14 and the edges 16 continuous as molded, but which may be easily torn or disrupted to free the tethers 14 from the edges 16. Adjacent ones of the tethers 14 are joined together at anchors 20 to provide ends of the tethers 14 that are anchored to the lid 10 and not easily torn or disrupted. A portion of the tethers 14 immediately adjacent the caps 12 is provided as a bend 14a that is not connected to the edges 16.

As molded, the tethers 14 are continuous with the edges 16 of the lid 10 and the caps 12 are substantially immobilized closely adjacent the edges 16 of the lid 10. As such, it has been observed that the lids 10 are more easily packaged, transported and stored than conventional lids and that the tethers do not tend to become entangled, as is the case with conventional lids.

Figure 2:
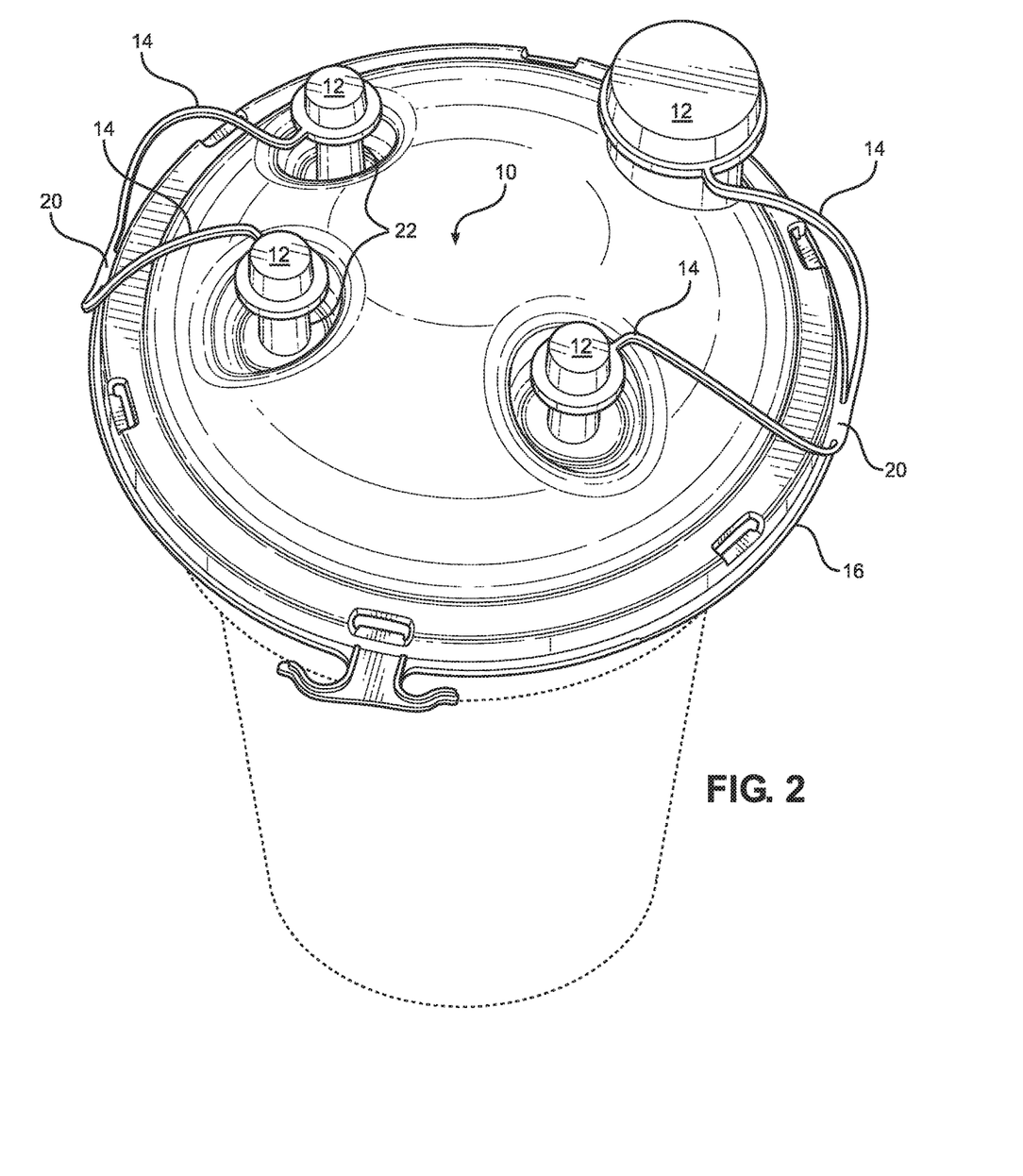
FIG. 2 depicts the canister lid of FIG. 1, with tethered caps thereof installed on ports of the lid.

FIG. 2 depicts the lid of FIG. 1 with the tethers 14 torn away from the edges 16 by application of hand pressure to disrupt the tear zones 18 to free the connection between the tethers 14 and the edges 16 so that the caps 12 may be installed on ports 22 of the lid 10. While each of the tethers 14 is shown torn away, it will be appreciated that the tear zones 18 for the tethers 14 for each of the caps 12 are independent. Thus, any one of the tethers 14 may be freed and cap 12 thereof utilized and the others left attached.

FIGS. 5A-5F depict tearing of one of the tear zones 18 to free one of the tethers 14 from the edge 16 so that the cap 12 associated therewith may be installed onto one of the ports 22 of the lid 10. The plastic of the tear zone 18 is configured to cleanly tear so that after the tether 14 is freed from the edge 16 of the lid 10, it is difficult to see any remnants of the tear zone 18. However, for the purpose of example, remnants of the plastic of the tear zone 18 are shown in the figures to illustrate that the plastic of the tear zone 18 is thin and that tearing has occurred to displace the tether 14. The tear zone 18 may be cut as by a razor blade instead of torn, but this is unnecessary as tearing is easily accomplished. For the lid 10 as shown, having a diameter of about 6½ inches, each of the tethers 14 have a length between the anchor 20 and the bend 14a of about 3 inches.

Figure 5A:
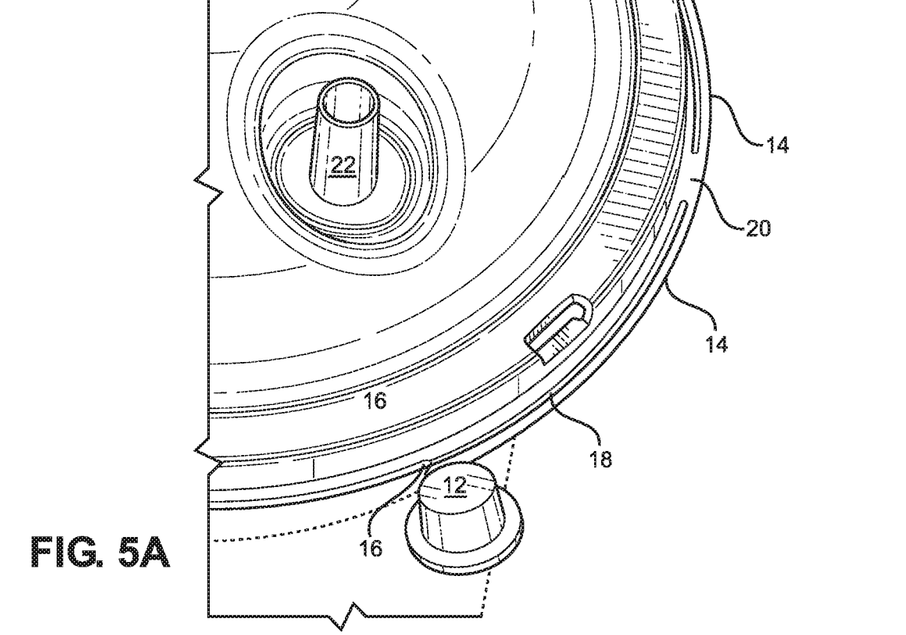
FIGS. 5A-5F depict tearing of a cap tether from the lid of FIG. 1.
Figure 5B:
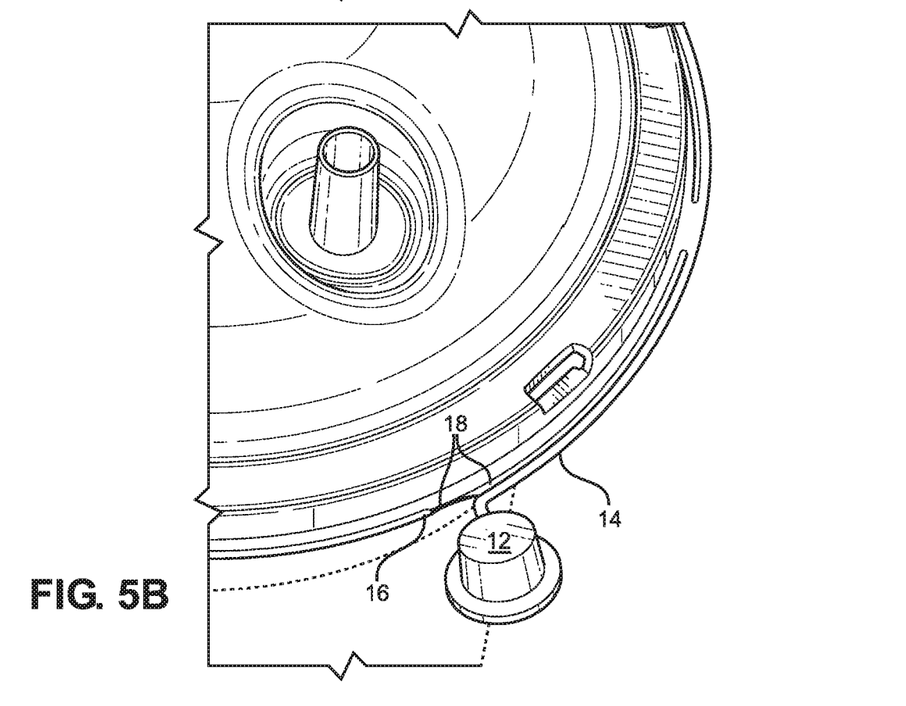
Figure 5C:
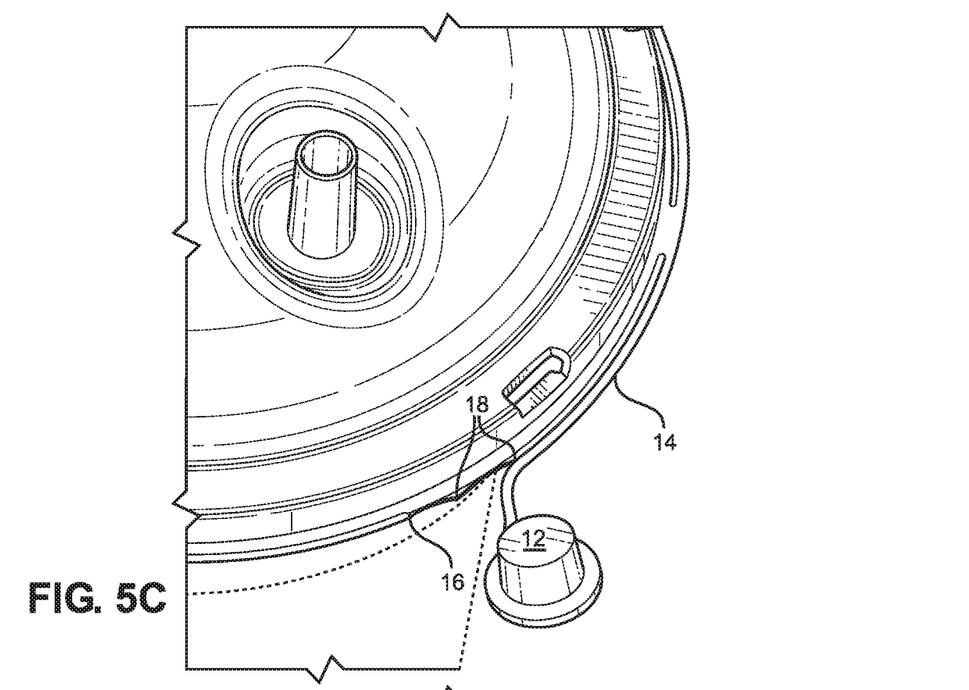
Figure 5D:
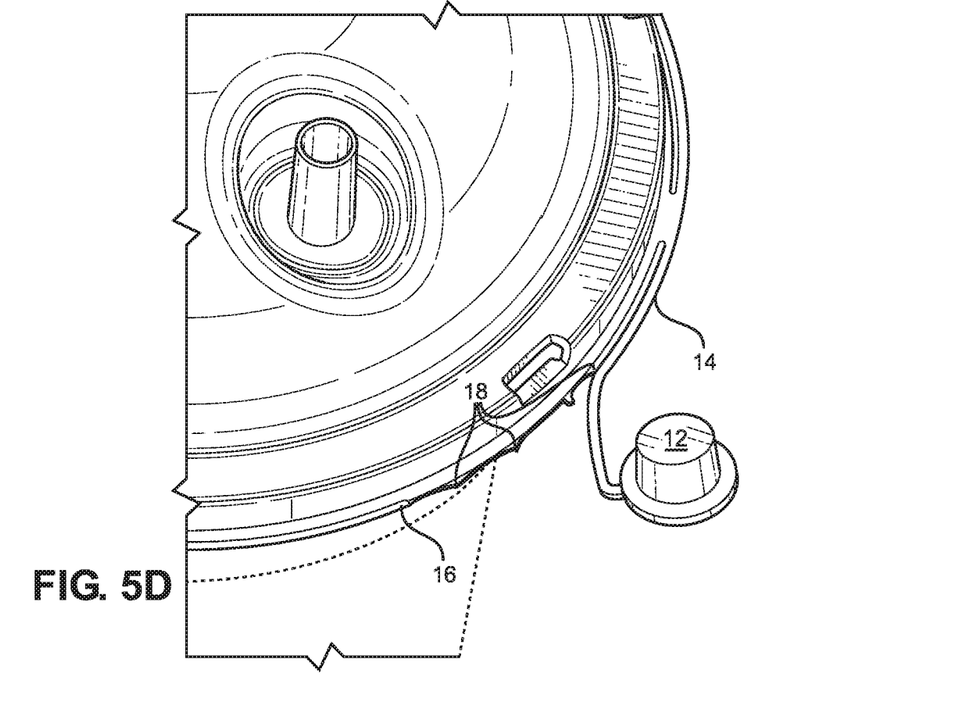
Figure 5E:
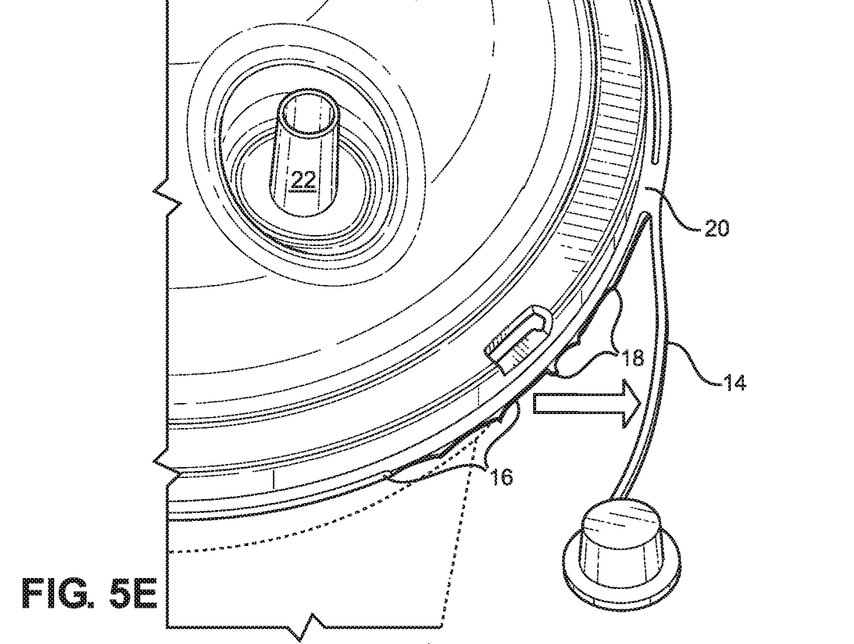
Figure 5F:
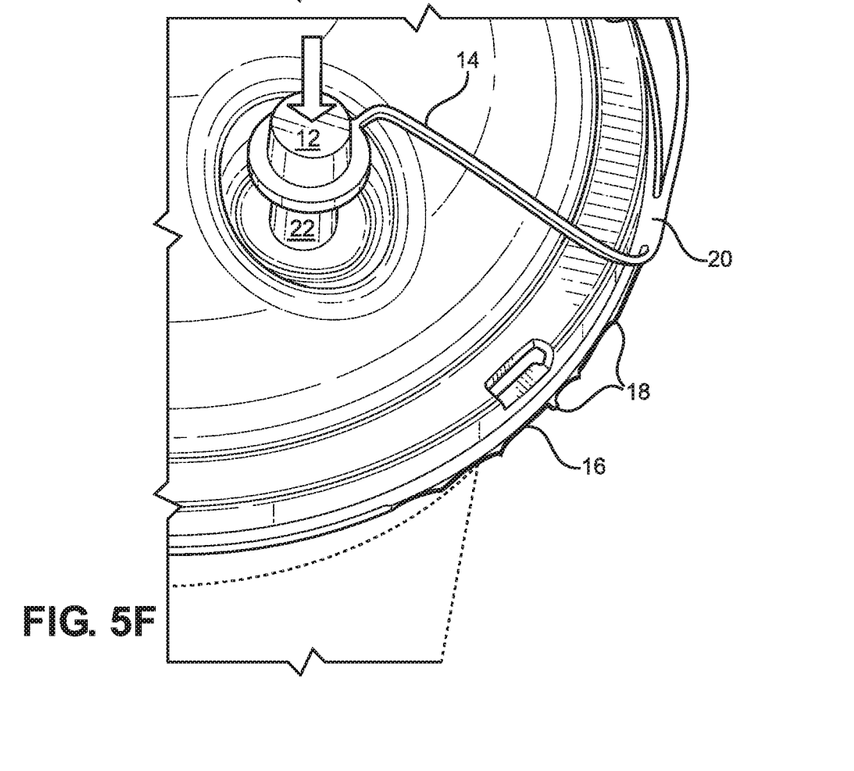

With reference to FIG. 5A, to initiate tearing of the tear zone 18, a user may grasp the cap 12 and pull the cap 12 outward, upward or preferably downward of the edge 16. Tearing pressure may be continued to tear the tear zone 18 until the entirety of the tear zone 18 has been torn. At this point, the tether 14 remains attached to the lid via the anchor 20. The tear zone has a thickness of about 1/64 inch and a width of about 1/64 inch.

The tether 14 is also relatively thin and narrow as compared to conventional tethers. As described previously, conventional thick tethers are usually at least about ⅛ inch in width and ⅛ inch in thickness. To the contrary, the tether 14 as shown has a width of about 1/16 inch and a thickness of about 1/16 inch to about ⅛ inch. This also advantageously renders the tether 14 significantly more pliable and flexible than conventional thick tethers. Thus, the tether 14 is more easily manipulated to orient the cap 12 onto the port 22 and the tether 14 does not tend to exert a force that urges the cap 12 away from the port 22. To the contrary, it has been observed that the dimensions of conventional thick tethers often result in the exertion of force that tends to pull the cap off the port.

Figure 6A:
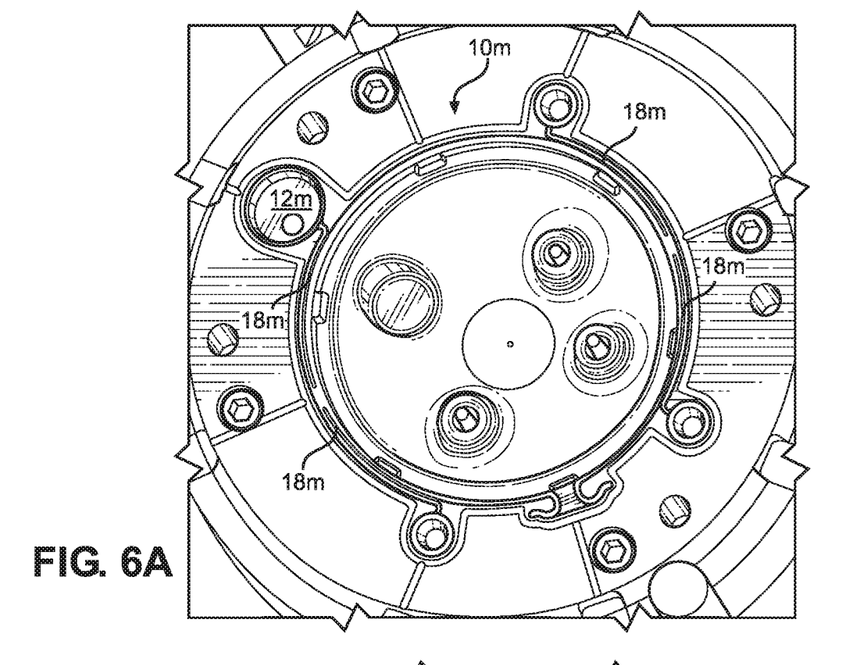
FIGS. 6A and 6B show aspects of molding of the cap of FIG. 1.
Figure 6B:
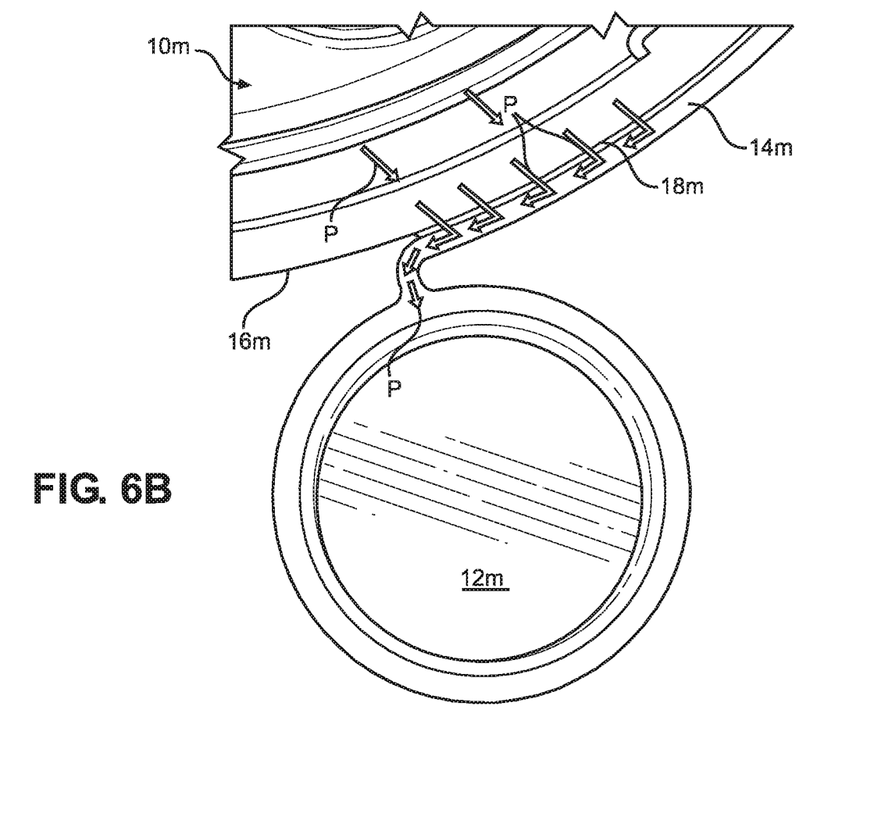

FIGS. 6A and 6B show aspects of molding of the cap of FIG. 1. FIG. 6A shows a mold 10m configured for molding the lid 10. A significant aspect of the mold 10m is that it includes a ridge 18m located where the tear zones 18 are formed in the lid 10. In this regard, the mold features of the mold 10m corresponding to the discussed parts of the lid 10 have corresponding m designations. For example, the mold features for the caps 12 are designated 12m, the mold features for the tethers 14 are designated 14m, and the mold features for the edges 16 are designated 16m. The ridges 18m correspond to mold features for the tear zones 18.

The ridge 18m occupies space between the mold features 12m, 14m, and 16m to restrict the accumulation of plastic during molding. However, as seen in FIG. 6B, flow of molten plastic during molding of the lid 10 using the mold 10m advantageously flows as represented by arrows P. Thus, the ridge 18m provides a path for plastic to flow directly from the edges 16m of the mold 10m to the mold features 12m and 14m.

This advantageously enables flow of plastic along the entire boundary of the edge features 16m and the tether mold features 14m to provide a large, low pressure flow path for the relatively large amount of plastic that must be supplied to the cap mold features 12m to form the caps 12. That is, while the path past the ridge 18m is of reduced dimension in thickness, it is a very wide path in that it spans most of the length of the tethers 14. Moreover, the presence of the ridge 18m causes the portions of the resulting lid 10 occupied by the ridges 18m to be thin and narrow to correspond to the tear zones 18, which are characterized as being very thin, tearable zones of plastic.

In contrast, in the manufacture of conventional caps, the tether paths are the only paths for plastic to flow to the cap mold features. Thus, the tether mold features must be wider and thicker. However, since the path is a long path, and still a relatively narrow plastic flow path for the flow of sufficient plastic to form a cap, relatively high pressures must be utilized, which results in correspondingly longer molding times.

Figure 7:
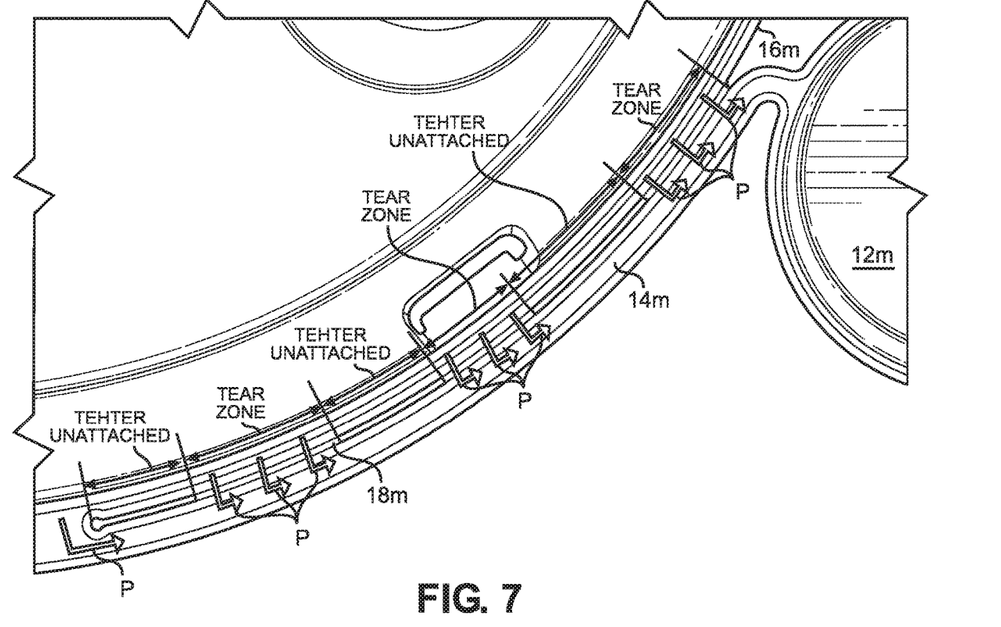
FIGS. 7 and 8 show alternate embodiments, in which tear lines are broken into segments instead of a continuous line along the tether length.
Figure 8:
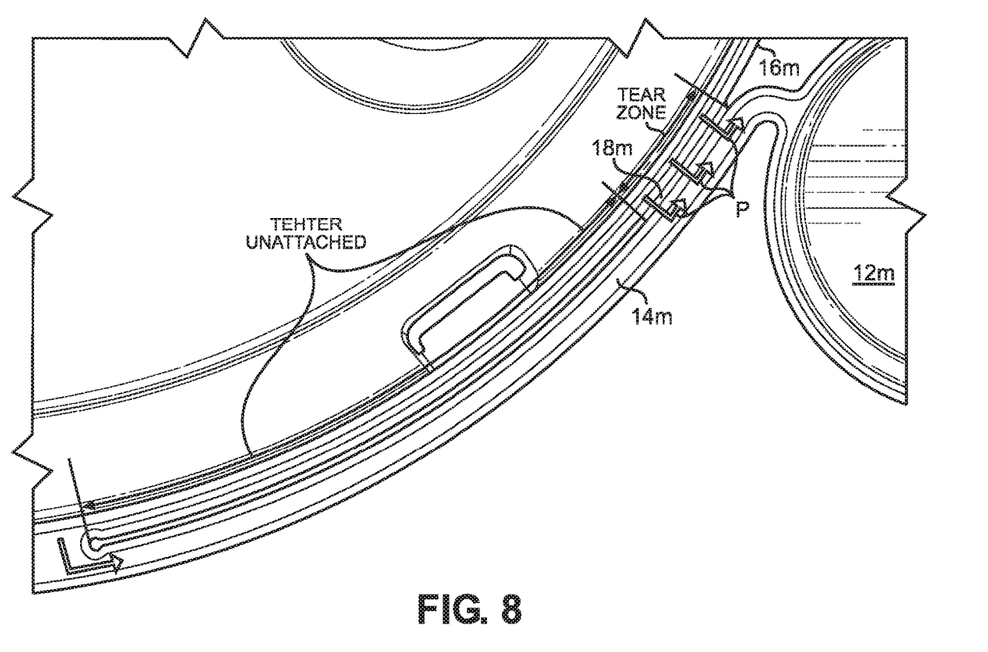

FIGS. 7 and 8 show alternate embodiments, in which the tear zones are not continuous along the length of the tether. In FIG. 7, the tear zone is shown as a plurality of spaced apart segments, with the locations therebetween being void of plastic. The embodiment of FIG. 8 shows an embodiment having a single tear zone proximate the cap, with the adjacent area toward the proximal portion of the tether being void of plastic. As will be appreciated, in each case, there are more plastic flow areas provided than for conventional tether molding, and the resulting tether is of reduced dimension.

Thus, as will be appreciated, the present structures, molded as described, may be made with lower pressures and shorter molding times. Further, as the resulting tethers 14 are considerably thinner, less plastic is utilized, and the thinner tethers have desirable characteristics as compared to conventional thick tethers, and the resulting lids are improved in not having tethers located from molding as to easily tangle and detract from packaging, transport and storage of the lids.

The foregoing description of preferred embodiments for this disclosure has been presented for purposes of illustration and description. It is not intended to be exhaustive or to limit the disclosure to the precise form disclosed. Obvious modifications or variations are possible in light of the above teachings. The embodiments are chosen and described in an effort to provide the best illustrations of the principles of the disclosure and its practical application, and to thereby enable one of ordinary skill in the art to utilize the disclosure in various embodiments and with various modifications as are suited to the particular use contemplated. All such modifications and variations are within the scope of the disclosure as determined by the appended claims when interpreted in accordance with the breadth to which they are fairly, legally, and equitably entitled.

The invention claimed is:

1. A mold for forming a lid having a cap connected to the lid by a tether, the mold having mold features for forming a lid body having a peripheral edge, a cap, a tether connecting the cap to the lid body, and a tear zone, the mold feature for forming the tear zone comprising an elongate ridge located between the mold feature for the tether and the mold feature for the lid body for providing a reduced thickness flow path proximate the ridge that connects between the mold feature for forming the lid body and the tether.

* * * * *